(12) United States Patent
Alabugin et al.

(10) Patent No.: US 9,206,100 B2
(45) Date of Patent: Dec. 8, 2015

(54) ROUTE TO SYNTHETIC ANALOGUES OF ROCAGLAMIDE AND AGLAFOLINE USING CASCADE TRANSFORMATIONS INITIATED BY OXY-COPE REARRANGEMENT OF BIS-ALKYNES

(75) Inventors: Igor Alabugin, Tallahassee, FL (US); Runa Pal, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 198 days.

(21) Appl. No.: 13/820,176

(22) PCT Filed: Sep. 13, 2011

(86) PCT No.: PCT/US2011/051299
§ 371 (c)(1),
(2), (4) Date: Mar. 1, 2013

(87) PCT Pub. No.: WO2012/037062
PCT Pub. Date: Mar. 22, 2012

(65) Prior Publication Data
US 2013/0165683 A1    Jun. 27, 2013

Related U.S. Application Data

(60) Provisional application No. 61/382,730, filed on Sep. 14, 2010.

(51) Int. Cl.
| | | |
|---|---|---|
| C07C 45/61 | (2006.01) | |
| C07C 29/68 | (2006.01) | |
| C07C 41/30 | (2006.01) | |
| C07C 41/32 | (2006.01) | |
| C07C 45/51 | (2006.01) | |
| C07C 45/68 | (2006.01) | |
| C07F 7/08 | (2006.01) | |

(52) U.S. Cl.
CPC .............. *C07C 29/68* (2013.01); *C07C 41/30* (2013.01); *C07C 41/32* (2013.01); *C07C 45/511* (2013.01); *C07C 45/61* (2013.01); *C07C 45/68* (2013.01); *C07F 7/083* (2013.01); *C07C 2101/10* (2013.01)

(58) Field of Classification Search
USPC ........................................................ 556/431
See application file for complete search history.

(56) References Cited

PUBLICATIONS

Paquette et al. J. Am. Chem. Soc. 1997, 119(6), 1230-1241.*
Pollart et al, J. Org. Chem., 1989, 54(23), 5444-8.*
Arns, Steve et al., Cascading pericyclic reactions: building complex carbon frameworks for natural product synthesis, Chem. Commun., 2007, pp. 2211-2221, The Royal Society of Chemistry.
Baldwin, Jack E. et al., Rules for Ring Closure: Application to Intramolecular Aldol Condensations in Polyketonic Substrates, Tetrahedron, 1982, pp. 2939-2947, vol. 38, No. 19, Great Britain.
Butenschon, Holger, Arene chromium complexes with functionalized anellated rings. Selective formation of hihgly substituted polycycles, Pure Appl. Chem., 2002, pp. 57-62; vol. 74, No. 1, IUPAC.
Carpenter, Barry K., A Simple Model for Predicting the Effect of Substituents on the Rates of Thermal Pericyclic Reactions, Tetrahedron, 1978, pp. 1877-1884, vol. 34, Pergamon Press Ltd.
Dahnke, Karl R. et al., Exploratory Synthetic Studies Involving the Tricyclo[9.3.0.02,8]tetradecane Ring System Peculiar to the Cyathins, J. Org. Chem., 1994, pp. 885-899, vol. 59, American Chemical Society.
Gentric, Lionel et al., Rate Acceleration of Anionic Oxy-Cope Rearrangements Induced by an Additional Unsaturation, Organic Letters, 2003, pp. 3631-3634, vol. 5, No. 20, American Chemical Society.
Graulich, Nicole et al., Heuristic thinking makes a chemist smart, Chemical Society Reviews, 2010, pp. 1503-1512, vol. 39, The Royal Society of Chemistry.
Huntsman, William D. et al., The Thermal Rearrangement of 1,5-Hexadiyne and Related Compounds, J. Org. Chem., Jan. 18, 1967, pp. 342-347, vol. 89, No. 2, Journal of the American Chemical Society.
International Search Report and Written Opinion of the International Searching Authority regarding PCT/US2011/051299 filed on Sep. 13, 2011 mailed on Mar. 26, 2012, pp. 10.
Evans, D.A. et al., [3,3] Sigmatropic Rearrangements of 1,5-Diene Alkoxides. The Powerful Accelerating Effects of the Alkoxide Substituent, Journal of the American Chemical Society, Aug. 6, 1975, pp. 4765-4766, vol. 97, No. 16, American Chemical Society.
Evans, D.A. et al., A General Approach to the Synthesis of 1,6 Dicarbonyl Substrates. New Applications of Base-Accelerated Oxy-Cope Rearrangements, Journal of the American Chemical Society, Mar. 29, 1978, pp. 2242-2244, vol. 100, No. 7, American Chemical Society.
Jacobi, Peter A. et al., Bis Heteroannulation. 7. Total Syntheses of (+)-Chididione and (+)-Isognididione, J. Am. Chem. Soc., 1987, pp. 3041-3043, vol. 106, Amerian Chemical Society.
Paquette, Leo A., Recent Applications of Anionic Oxy-Cope Rearrangements, Tetrahedron Report No. 429, 1997, pp. 13971-14020, vol. 52, No. 41, Elsevier Science Ltd, Great Britian.
Roth, Wolfgang R. et al., A "Frustrated" Cope Rearrangement: Thermal Interconversion of 2,6-Diphenylhepta-1,6-diene and 1,5-Diphenylbicyclo[3.2.0]heptain, Journal of the American Chemical Society, 1990, pp. 1722-1732, vol. 112, American Chemical Society.
Pal, Runa et al., Fast Oxy-Cope Rearrangements of Bis-alkynes: Competition with Central C-C Bond Fragmentation and Incorporation in Tunable Cascades Diverging from a Common Bis-allenic Intermediate, JOC Note, 2010, pp. 8689-8692, vol. 75, J. Org. Chem.
Zimmerman, Howard E., Kinetic Protonation of Enols, Enolates, and Analogues. The Stereochemistry of Ketonization, Acc. Chem. Res., 1987, pp. 263-268, vol. 20, American Chemical Society.
Zimmerman, Howard E. et al, The Stereochemistry of Allenic Enol Tautomerism—Independent Generation and Reactivity of he Enolates, Eur. J. Org. Chem., 2006, pp. 3491-3497, Wiley-VCH Verlag GmbH & Co.

* cited by examiner

*Primary Examiner* — Yong Chu
*Assistant Examiner* — Ana Z Muresan
(74) *Attorney, Agent, or Firm* — Armstrong Tesadale LLP

(57) ABSTRACT

A method for preparing a cyclobutene compound or a cyclopentenone is provided. The method comprises contacting an α,β-diketone with a metal acetylide at a temperature below 0° C. to thereby form a reaction mixture comprising a bis-alkyne precursor. The bis-alkyne precursor rearranges into a bis-allenic intermediate, which undergoes further rearrangement into the cyclobutene compound or the cyclopentenone compound as the temperature of the reaction mixture increases from below 0° C. to above 0° C.

20 Claims, 4 Drawing Sheets

ROUTE TO SYNTHETIC ANALOGUES OF ROCAGLAMIDE AND AGLAFOLINE USING CASCADE TRANSFORMATIONS INITIATED BY OXY-COPE REARRANGEMENT OF BIS-ALKYNES

CROSS REFERENCE TO RELATED APPLICATIONS

This application is a U.S. national stage application based on PCT/US2011/051299, filed on Sep. 13, 2011, which claims priority from U.S. provisional application Ser. No. 61/382,730, filed on Sep. 14, 2010, the entire contents of each of which is hereby incorporated herein by reference.

STATEMENT REGARDING FEDERALLY SPONSORED RESEARCH

This invention was made with Government support under Grant CHE-0848686 awarded by the National Science Foundation. The Government has certain rights in this invention.

FIELD OF THE INVENTION

The present invention generally relates to an efficient method for the preparation of a functionalized cyclobutene compound or a cyclopentenone compound. More specifically, the preparation of a functionalized cyclobutene or cyclopentenone compound proceeds via cascade transformations which originate from a bis-allenic intermediate provided via anionic oxy-Cope rearrangement of bis-alkynes.

BACKGROUND OF THE INVENTION

Efficient control of the Cope rearrangement and related reactions is important for incorporation of this useful C—C bond forming method in subsequent reaction cascades, especially if these cascades have to be tunable. See (a) H. Hopf, Classics in hydrocarbon chemistry; Wiley-VCH: Weinheim, Germany, 2000; pp 11-14. (b) S. Arns, L. Barriault, Chem. Comm. 2007, 22, 2211. (c) H. Butenschön, Pure Appl. Chem. 2002, 74, 57. (d) P. A. Jacobi, H. G. Selnick, J. Am. Chem. Soc. 1984, 106, 3041. (e) L. A. Paquette, Tetrahedron. 1997, 53, 13971 (f) K. R. Dahnke, L. A. Paquette, J. Org. Chem. 1994, 59, 887. (g) L. A. Paquette, S. J. Bailey, J. Org. Chem. 1995, 46, 2199. (h) L. Barriault, D. H. Deon, Org. Lett. 2001, 3, 1925. Extensive experimental and computational data suggests that the rearrangement transition state is very sensitive to the nature and position of substituents. See (a) W. von E. Doering, Y. Wang, J. Am. Chem. Soc. 1999, 121, 10112. (b) W. von E. Doering, Y. Wang, J. Am. Chem. Soc. 1999, 121, 10967. (c) W. von E. Doering, L. Birladeanu, K. Sarma, G. Blaschke, U. Scheidemantel, R. Boese, J. Benet-Bucholz, F.-G. Klärner, J. S. Gehrke, B. U. Zinny, R. Sustmann, H.-G. Korth, J. Am. Chem. Soc. 2000, 122, 193. (d) L. Gentric, I. Hanna, A. Huboux, R. Zaghdoudi, Org. Lett. 2003, 5, 3631. (e) V. N. Staroverov, E. R. Davidson. J. Am. Chem. Soc. 2000, 122, 186. (f) D. A. Hrovat, B. R. Beno, H. Lange, H.-Y. Yoo, K. N. Houk, W. T. Borden, J. Am. Chem. Soc. 1999, 121, 10529. (g) D. A. Hrovat, J. Chen, K. N. Houk, W. T. Borden, J. Am. Chem. Soc. 2000, 122, 7456. For example, Evans reported a dramatic acceleration of the Oxy-Cope rearrangement via introduction of anionic substituents while Doering and others controlled the electronic character of the Cope transition state with appropriately positioned Ph-groups. See (a) D. A. Evans, A. M. Golob, J. Am. Chem. Soc. 1975, 97, 4765. (b) B. K. Carpenter, Tetrahedron. 1978, 34, 1877. (c) D. A. Evans, D. J. Ballallargeon, J. V. Nelson, J. Am. Chem. Soc. 1978, 100, 2242. (d) W. R. Roth, H-W Lennartz, W. v E. Doering, L. Birladeanu, C. A. Guyton, T. Kitagawa, J. Am. Chem. Soc. 1990, 112, 1722.

The rich mechanistic spectrum of reactions "under the umbrella of Cope rearrangement family" was further illustrated by predictions of unusual Cope rearrangement patterns based on comprehensive heuristic approach. See A. Navarro-Vazquez, M. Prall, P. R. Schreiner, Org. Lett. 2004, 6, 2981. Graulich, N.; Hopf, H.; Schreiner, P. R. Chem. Soc. Rev. 2010, 39, 1503. Earlier computational evidence suggested that some anionic Cope rearrangements proceed via a dissociative mechanism initiated by a homolytic cleavage of the central C—C bond. See (a) K. A. Black, S. Wilsey, K. N. Houk, J. Am. Chem. Soc. 1998, 120, 5622. (b) Y. Y. Hi, K. N. Houk, J. Am. Chem. Soc. 1998, 120, 205. (c) K. A. Black, S. Wilsey, K. N. Houk, J. Am. Chem. Soc. 2003, 125, 6715.

During the past few years, a group of cyclopenta[b]benzofurans from the plant genus Aglaia has received broad scientific attention as interesting natural product lead compounds with potential anticancer and insecticidal activities. Rocaglamide (Roc), derived from the traditional Chinese medicinal plants Aglaia, induces apoptosis through the intrinsic death pathway in various human leukemia cell lines and in acute lymphoblastic leukemia, chronic myeloid leukemia and acute myeloid leukemia cells freshly isolated from patients. Rocaglamide belongs to the group of 1H-cyclopenta[b]benzofurans. It has been demonstrated that they possess antiproliferative activity. And also have been shown to have an inhibitory effect on growth of a murine leukaemia cell line (P-388) and a human breast cancer cell line (BCl) in vitro and also in vivo.

Over 40 cyclopenta[b]benzofurans have been tested against different human cancer cell lines, and the cumulative results suggest that it is possible to improve their activity through chemical modification. Studies of these compounds on their cellular mechanism of action have demonstrated that some of these compounds inhibit TNF-a or PMA-induced NF-kB activity in T-lymphocytes and induce apoptosis in different human cancer cell lines. Based on the published data thus far, cyclopenta[b]benzofurans offer excellent starting platform for the design of therapeutic agent candidates in cancer chemotherapy.

There are several literature reports that can lead to the synthesis of Rocaglamide, Aglafoline, and their analogues, but all of these approaches involve multi-step synthesis. Several of these approaches are shown below.

Synthesis of rocaglaol/rocaglamide from benzofurane by Taylor et al. (33% overall yield):

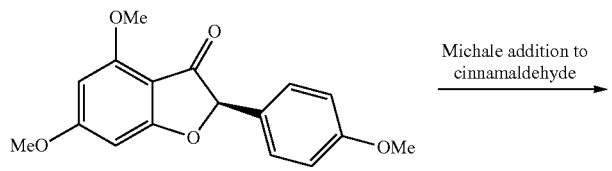

Michale addition to cinnamaldehyde

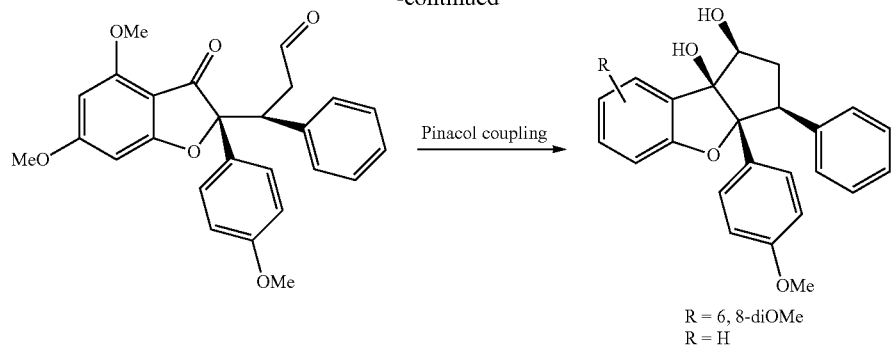

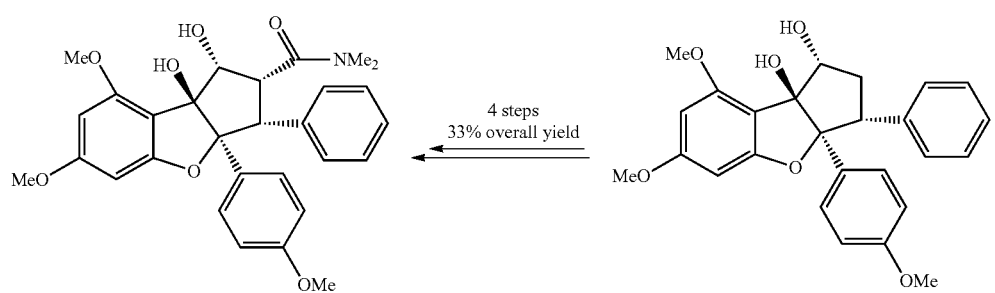

Frontier et al. reported the synthesis of Rocaglamide/Aglafoline in 13 and 11 steps, respectively from known benzofuranone. The key transformation is Nazarov cyclization of a pentadienyl cation generated in an unusual way: through peracid oxidation of an allenol ether.

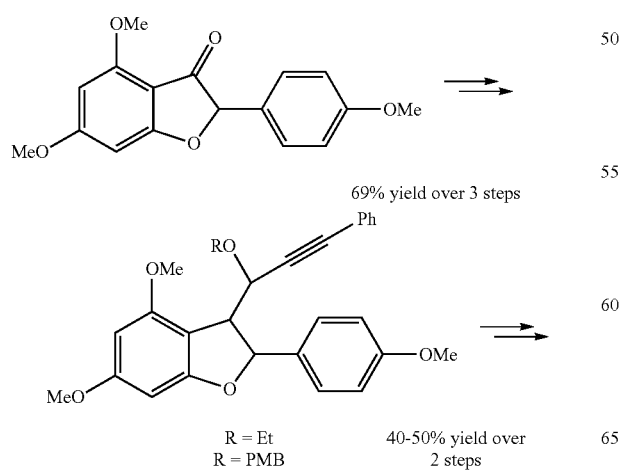

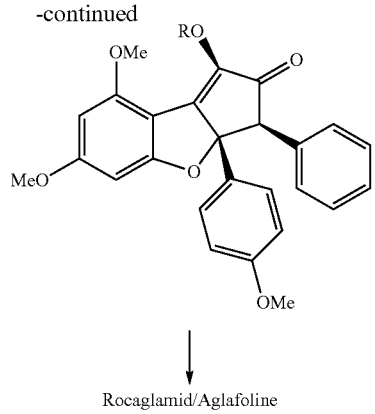

Another approach involves multistep synthesis of cyclopentenone with overall 36% yield via intramolecular epoxide opening.

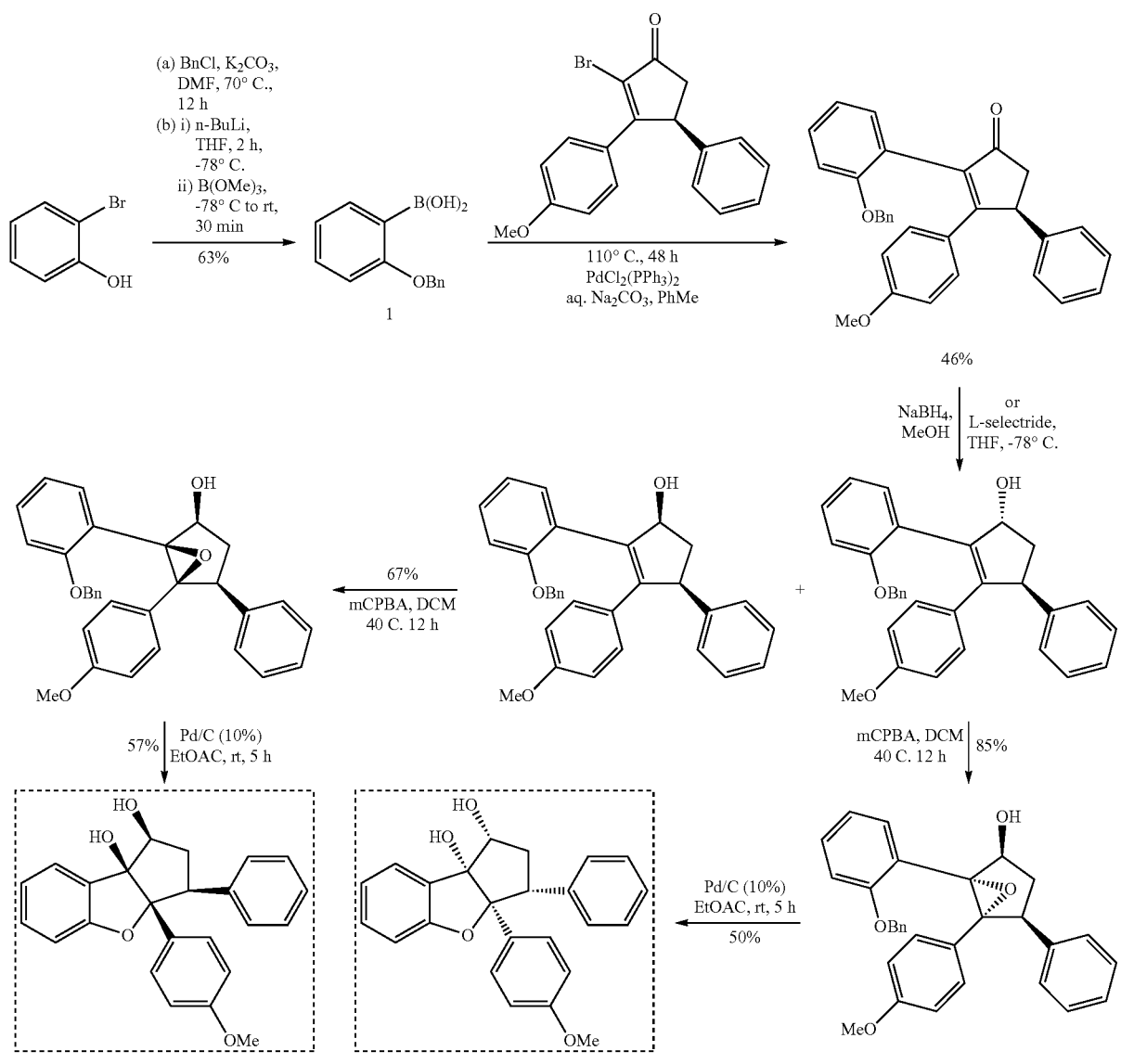

SUMMARY OF THE INVENTION

Briefly, the present invention is directed to a method of preparing a cyclobutene compound. The method comprises contacting an α,β-diketone with a metal acetylide at a temperature below 0° C. to thereby form a reaction mixture comprising a bis-alkyne precursor. The bis-alkyne precursor rearranges into a bis-allenic intermediate, which undergoes further rearrangement into the cyclobutene compound as the temperature of the reaction mixture increases from below 0° C. to above 0° C.

The present invention is additionally directed to a method of preparing a cyclopentenone compound. The method comprises contacting an α,β-diketone with a metal acetylide at a temperature below 0° C. to thereby form a reaction mixture comprising a bis-alkyne precursor. The bis-alkyne precursor rearranges into a bis-allenic intermediate, which undergoes further rearrangement into the cyclopentenone compound as the temperature of the reaction mixture increases from below 0° C. to above 0° C.

Other objects and features will be in part apparent and in part pointed out hereinafter.

DESCRIPTION OF THE EMBODIMENT(S) OF THE INVENTION

Figure 1A:
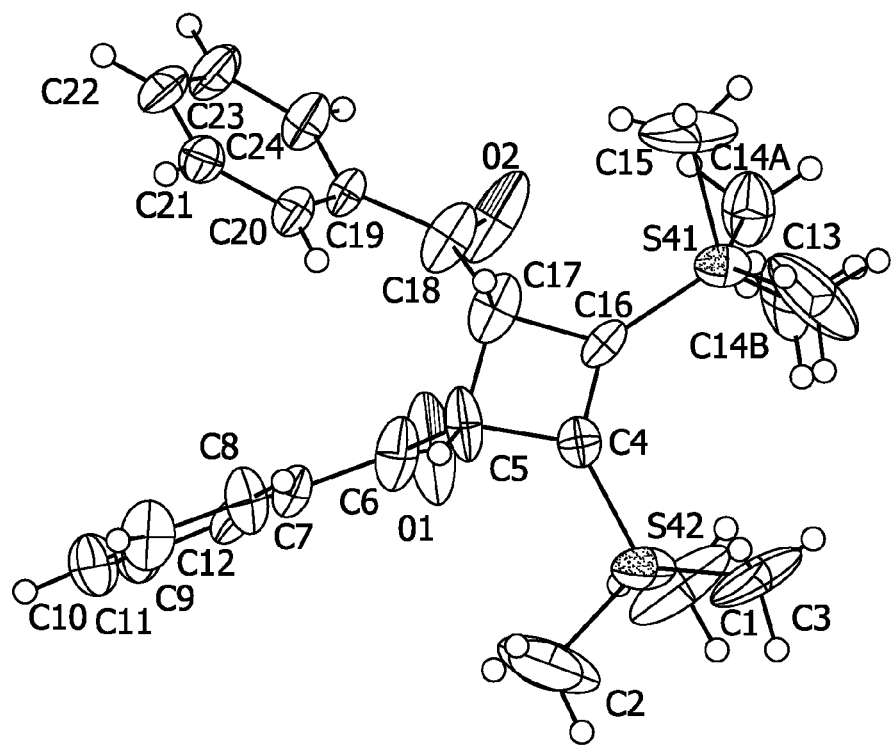
FIG. 1A is an ORTEP diagram for a cis-isomer (3-TMS-cis) cyclobutene compound prepared according to the method of the present invention.

The method of the present invention is directed to a cascade reaction that yields highly functionalized compounds. In particular, the present invention is directed to a method that efficiently and conveniently prepares cyclobutene and cyclopentenone compounds via a common bis-allenic intermediate. Advantageously, the method of the present invention avoids expensive and toxic reagents. Additionally, the method of the present invention yields highly functionalized compounds with overall high yield of (75-85%).

The bis-allenic intermediate may be prepared by the reaction of α,β-diketone, e.g., 1,4-diphenyl-2,3-ethanedione (benzil), with two stoichiometric equivalents of metal acetylides, which forms a bis-alkyne precursor. In general, the reaction, which prepares the precursor occurs at temperatures below about 0° C. It has been observed that the bis-alkyne intermediate readily rearranges into a bis-allenic intermediate via oxy-Cope rearrangement as the reaction mixture warms to the room temperature. The bis-allenic intermediate further rearranges into a cyclobutene or a cyclopentenone compound that is heavily substituted and functionalized. The compounds prepared according to the method of the present invention may represent useful intermediates in the product of analogues of cytotoxic compounds, such as Rocaglamide and Aglafoline.

The method of the present invention is directed to the preparation of a functionalized cyclobutene or a functionalized cyclopentenone. The transformation proceeds via a cascade transformation which originates from a common bis-allenic intermediate. The common bis-allenic intermediate is the product of anionic oxy-Cope rearrangement of a bis-alkyne precursor. With this one-pot synthesis, it is possible to access new biologically active molecules in an expedient and cost-efficient fashion. For example, the method of the present invention is useful in the preparation of a functionalized cyclopentenone that may serve as a starting material in the synthesis of Rocaglamide and Aglafoline analogues, natural compounds which have shown cytostatic and cytotoxic activity against a variety of human cancer cell lines with IC50 values ~1.0-6.0 ng/mL. In view thereof, the method of the present invention is useful in the preparation of starting materials for the synthesis of a wide variety of compounds potentially useful in the treatment of cancer.

The method of the present invention may advantageously be carried out as a one-pot synthesis enabling the introduction of molecular complexity which transforms readily available starting materials (e.g., benzil and a metal acetylide) into densely functionalized cyclic compounds such as functionalized cyclobutenes and functionalized cyclopentenones. The nature of the product, e.g., cyclobutene or cyclopentenone, is dependent in part on the nature of substituents at an acetylenic moiety of a starting material.

The overall method of the present invention may be exemplified according to the following reaction Scheme 1 showing specific reactants, e.g., 1,2-diphenylethane-1,2-dione (commonly known as benzil) reacted with 2 equivalents lithium acetylide, and an array resulting products, including fragmentation products, cyclobutene products, cyclopentenone products, and linear conjugated products. The pathway of the invention and the final resultant product(s) is determined via the selection of particular R moieties on the metal acetylide reactant:

Scheme 1:

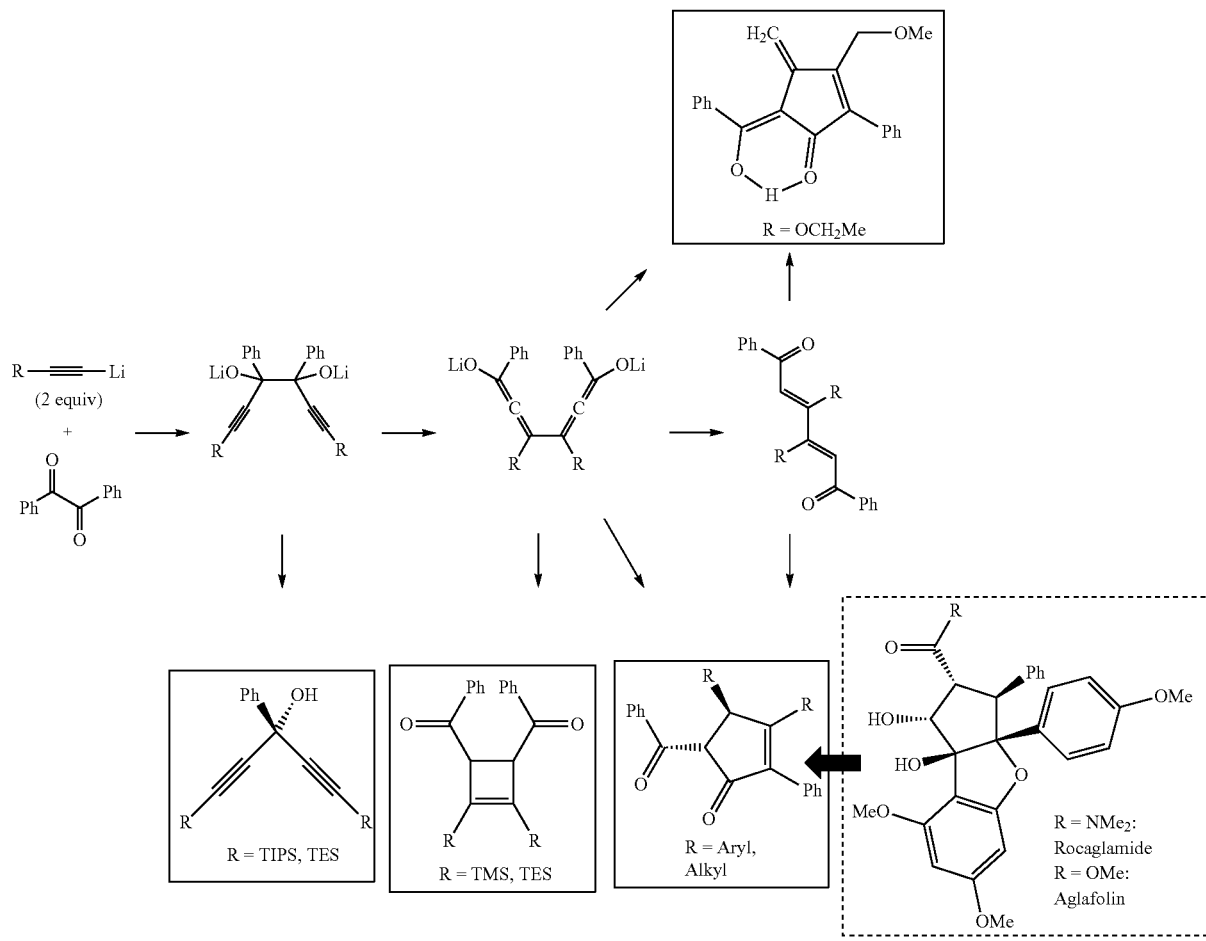

The above Scheme 1 demonstrates that a variety of reaction pathways are possible by reacting an α,β-diketone (benzil is shown) with two equivalents of a metal acetylide (a lithium acetylide is shown). Scheme 1 thus shows the tunability of the method of the present invention. The progress of the reaction depends upon the identity of the R group on the metal acetylide reactant.

In the first step, a bis-alkyne precursor is formed by the reaction of the α,β-diketone (benzil is shown) with two equivalents of a metal acetylide. In some embodiments, the nature of R group causes the reaction to proceed such that the bis-alkyne to fragment into, e.g., geminal bis-alkyne alcohols. In some embodiments, the nature of R group causes the reaction to proceed such that the bis-alkyne rearranged via an Oxy Cope mechanism into a bis-allenic intermediate. The bis-allenic intermediate further rearranges into a functionalized cyclobutene, a functionalized cyclopentenone, or a linear conjugated compound.

When using silyl-substituted alkynes, either the bis-alkyne precursor fragments via a dissociative pathway into fragmentation products (i.e., when the silyl groups are bulky) or the bis-alkyne precursor rearranges into a bis-allenic intermediate that further rearranges into a cyclobutene. When using alkyl- and aryl-substituted alkynes, the bis-allenic intermediate may be transformed into cyclopentenone products.

The following reaction Scheme 2 illustrates the same reactions shown in Scheme 1 by breaking down the cascades into steps. In the steps illustrated in Scheme 2, certain carbons are labeled (1, 2, 3, 1', 2', and 3') to show correspondence between carbon atoms in the reactants, the bis-alkyne precursor, the bis-allenic intermediate, and the reaction products.

Scheme 2:

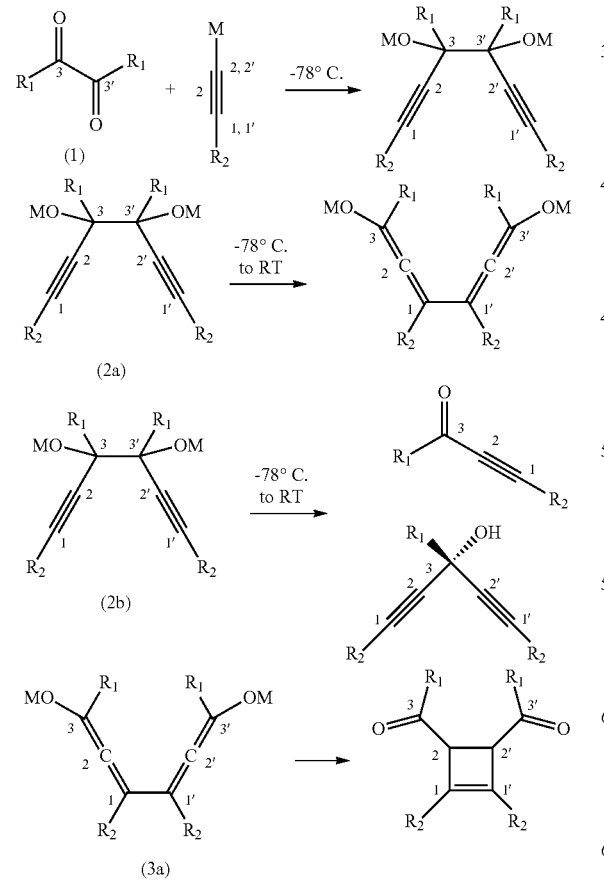

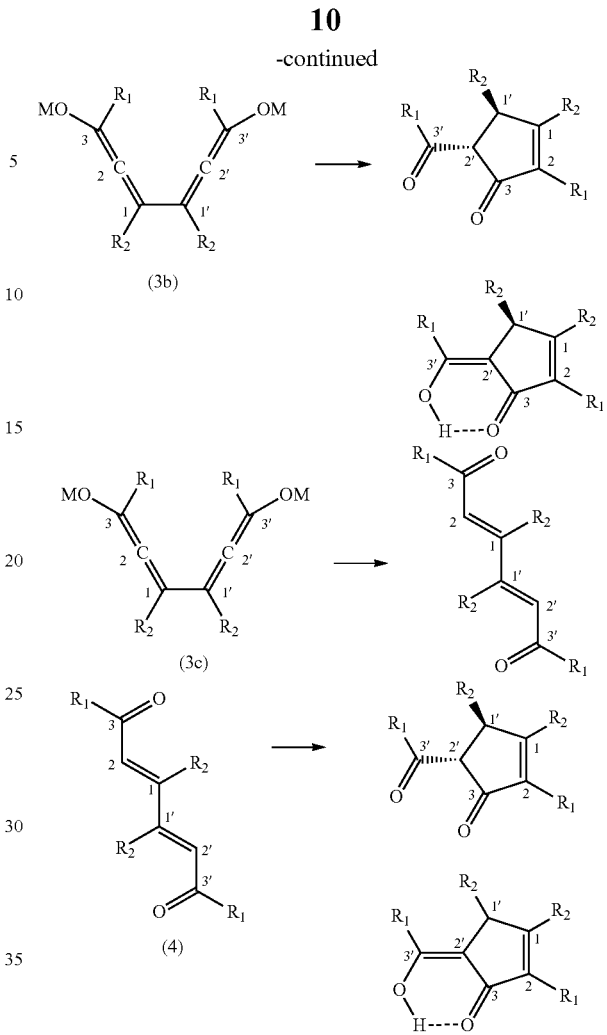

As illustrated by Scheme 2, the method of the present invention includes a step (1) in which an α,β-diketone is contacted with a metal acetylide at a temperature below about 0° C. to thereby form a reaction mixture comprising a bis-alkyne precursor.

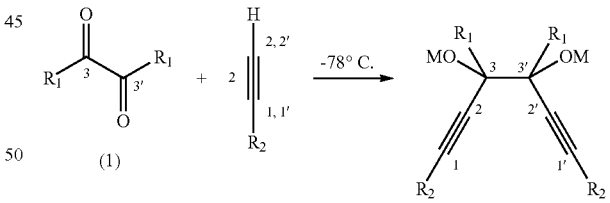

The reaction is generally carried out in aprotic solvents, such as tetrahydrofuran, diethylether, dichloromethane, ethylacetate, acetone, dimethylformamide, acetonitrile, and dimethylsulfoxide. In preferred embodiments, the solvent comprises tetrahydrofuran.

The α,β-diketone has the general structure:

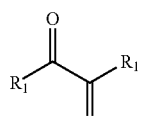

wherein $R_1$ is a hydrocarbyl generally having from 1 to about 18 carbon atoms, preferably from 1 to about 12 carbon atoms, more preferably from 1 to about 6 carbon atoms. The hydrocarbyl may be an alkyl, alkenyl, alkynyl, cycloalkyl, aryl, or alkylaryl. Exemplary $R_1$ groups include methyl, phenyl, ethyl, n-propyl, isopropyl, n-butyl, isobutyl, tert-butyl, pentyls, hexyls, and cyclohexyls. The hydrocarbyls may be substituted or unsubstituted.

In some embodiments of the present invention, both $R_1$ groups are phenyl, which may be substituted or unsubstituted. Substituents groups on the phenyl may be alkyl, aryl, and alkoxy substituents at any of the ortho-, meta-, and para-positions. In general, the substituents may have from 1 to 12 carbon atoms, preferably from 1 to 6 carbon atoms. Exemplary substituents on the phenyl group include methyl, ethyl, propyl, methoxy, ethoxy, propoxy, and phenyl substituents.

In some preferred embodiments of the method of the present invention, both $R_1$ are phenyl and the $\alpha,\beta$-diketone is 1,2-diphenylethane-1,2-dione (commonly known as benzil), which has the following structure:

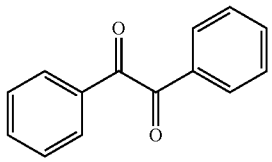 [SMILES: O=C(C(=O)c1ccccc1)c1ccccc1]

The metal acetylide has the following structure:

wherein M is a counterion, generally an alkali metal cation such as lithium cation, sodium cation, or potassium cation. In preferred embodiments, M is a lithium cation. The identity of $R_2$ is selected according to the desired final product of the reaction. That is, the identity of $R_2$ determines whether the final product is a fragmentation product, a cyclobutene, a linear conjugate, or a cyclopentenone. In some embodiments, a mixture of products may result from the cascade reaction. For example, in some embodiments, the $R_2$ group may influence the cascade such that a mixture of fragmentation products and cyclobutene products results. In some embodiments, the $R_2$ group may influence the cascade such that a mixture of cyclopentenone products results or a mixture of cyclopentenone and linear conjugates result. $R_2$ groups may be selected from among silyl moieties, alkyl moieties, and aryl moieties. Exemplary and non-limiting $R_2$ groups include trimethylsilyl (TMS), triethylsilyl (TES), tri-isopropyl silyl (TIPS), phenyl, tolyl, para-fluorophenyl, and —$CH_2$—O—$CH_3$.

In the method of the present invention, the metal acetylide may be added to the reaction mixture or may be prepared in situ. In some preferred embodiments, the metal acetylide is prepared in situ, such as according to the following reaction sequence, which prepares a lithium acetylide:

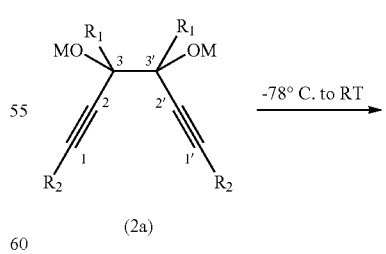

In some embodiments of the method of the present invention, the $\alpha,\beta$-diketone is contacted with the metal acetylide at a molar ratio of metal acetylide to $\alpha,\beta$-diketone of at least about 1.9:1, more preferably at least about 1.95:1, even more preferably the molar ratio of metal acetylide to $\alpha,\beta$-diketone is at least about 2.0:1. Excess metal acetylide may be achieved by adding a molar excess of the acetylide compound and preparing the metal acetylide in situ with butyllithium or lithium bis(trimethylsilyl)azanide. The reaction is generally carried out in aprotic solvents, such as tetrahydrofuran, diethylether, dichloromethane, ethylacetate, acetone, dimethylformamide, acetonitrile, and dimethylsulfoxide.

The reaction to prepare the bis-alkyne precursor occurs below about 0° C., preferably below about –20° C., even more preferably below about –50° C., such as –78° C. Such temperature may be achieved, for example, by immersing the reaction vessel in an acetone/dry ice bath.

In some preferred embodiments of the method of the present invention, the bis-alkyne precursor may be prepared conveniently via reaction of 1,4-diphenyl-2,3-ethanedione (benzil) with two equivalents of metal acetylides:

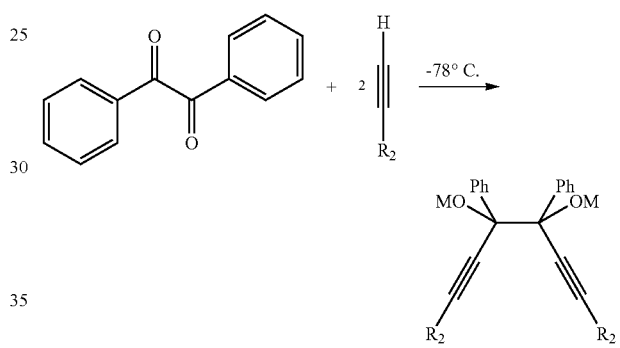

According to the method of the present invention, as illustrated in Scheme 2, the bis-alkyne precursor prepared via the reaction between an $\alpha,\beta$-diketone and a metal acetylide undergoes anionic oxy Cope rearrangement to a bis-allenic intermediate or alternatively may undergo rearrangement into fragmentation products. The direction of the method depends upon the nature of the $R_2$ groups on the metal acetylide. This rearrangement occurs in situ as the temperature of the reaction mixture increases from a temperature below 0° C., e.g., the preferred temperature of –78° C., to a temperature above 0° C., e.g., ambient room temperature.

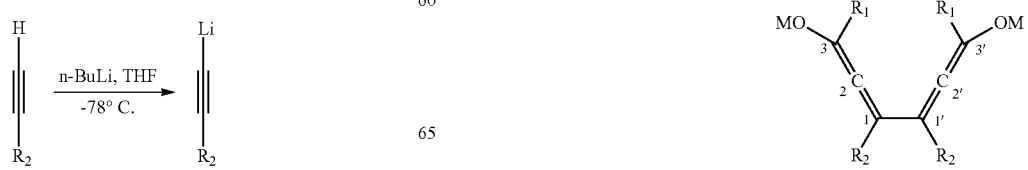

(2a)

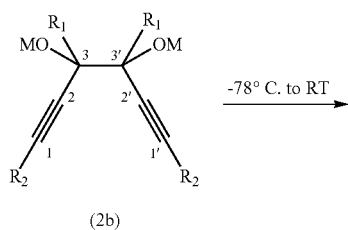

(2b)

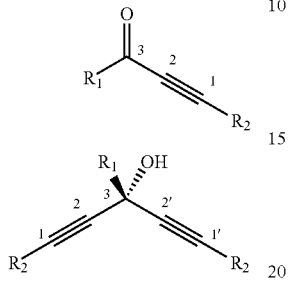

Remarkably, oxy-Cope rearrangement of the resulting bis-alkyne precursor into the bis-allenic intermediate or fragmentation occurs readily as the reaction mixture warms to the room temperature. In preferred embodiments wherein the α,β-diketone is 1,4-diphenyl-2,3-ethanedione (benzil; both $R_1$ groups are phenyl), the Ph groups weaken the central C—C bond in the bis-alkyne intermediate and provide additional thermodynamic stabilization to the newly formed C=C bonds in the bis-allenic intermediate product.

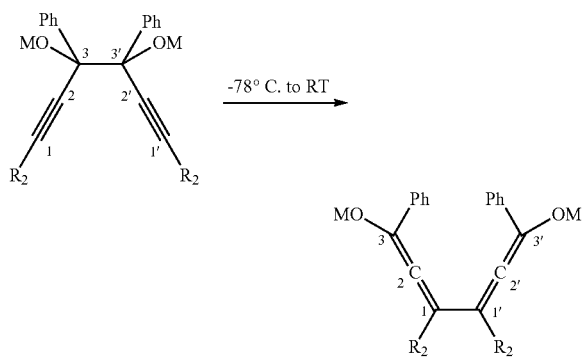

Subsequent rearrangement of the bis-allenic oxy-Cope intermediate products can be controlled efficiently by the nature of substituents in the acetylenic nucleophiles. Depending on the alkyne, i.e., the identity of the $R_2$ groups, divergent anionic cascades of the bis-allenic intermediates either transform simple acyclic starting materials into densely functionalized cyclobutene and cyclopentenone products or follow fragmentation products via a dissociative pathway. In view thereof, the bis-allenic intermediate formed in situ may be tailored with functionality that determines the nature of the cyclic product.

In embodiments wherein a cyclobutene is desired, the $R_2$ substituent of the metal acetylide contains silyl functionality. In some embodiments, the $R_2$ substituent comprises trimethylsilyl (TMS). In some embodiments, the $R_2$ substituent comprises triethylsilyl (TES). The general reaction sequence to prepare a cyclobutene is shown below in the following Scheme 3 ($R_2$ may be TMS or TES):

Scheme 3:

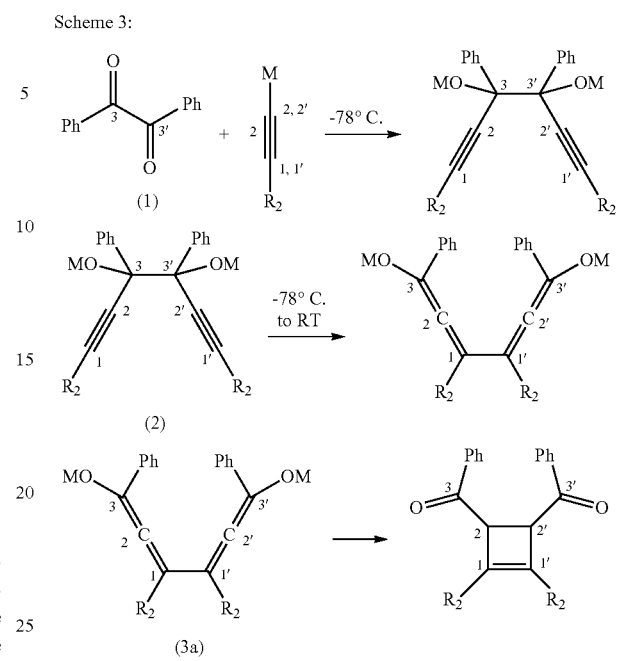

In one embodiment, a bis-allenic intermediate formed in situ by the reaction of benzil with TMS-substituted ($R_2$=tetramethylsilane ("TMS")) acetylide undergoes rapid 4π-electrocyclic closure to a mixture of cis- and trans-cyclobutenes 3-TMS in an ~80% overall yield. An analogous cascade of 1,5-hexadiyne proceeds only at temperatures>250° C.: W. D. Huntsman, H. J. Wristers, *J. Am. Chem. Soc.* 1967, 89, 342.

The structure of the cis-isomer (3-TMS-cis) was confirmed by X-ray crystallography. See FIG. 1a. However, 4π-electrocyclization was not able to compete with ketonization of bis-allenol formed in the oxy-Cope rearrangement of a 1,5-hexadiyne-3,4-diol. See (a) N. Manisse, J. Chuche, *Tetrahedron,* 1975, 35, 3095 and (b) A. Viola, J. J. Collins, N. Filipp, *Tetrahedron.* 1981, 37, 3765.

The cis isomer is initially present as the major product in the reaction mixture (~10:1 cis:trans selectivity). See Scheme 4:

SCHEME 4:

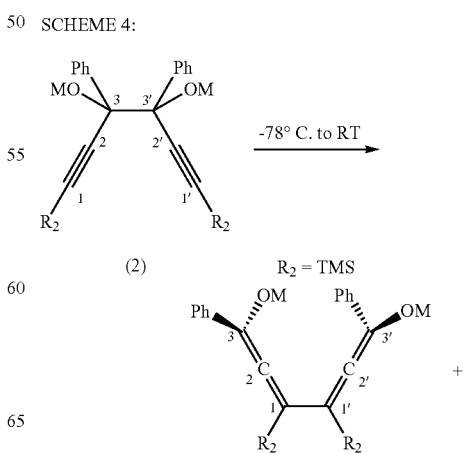

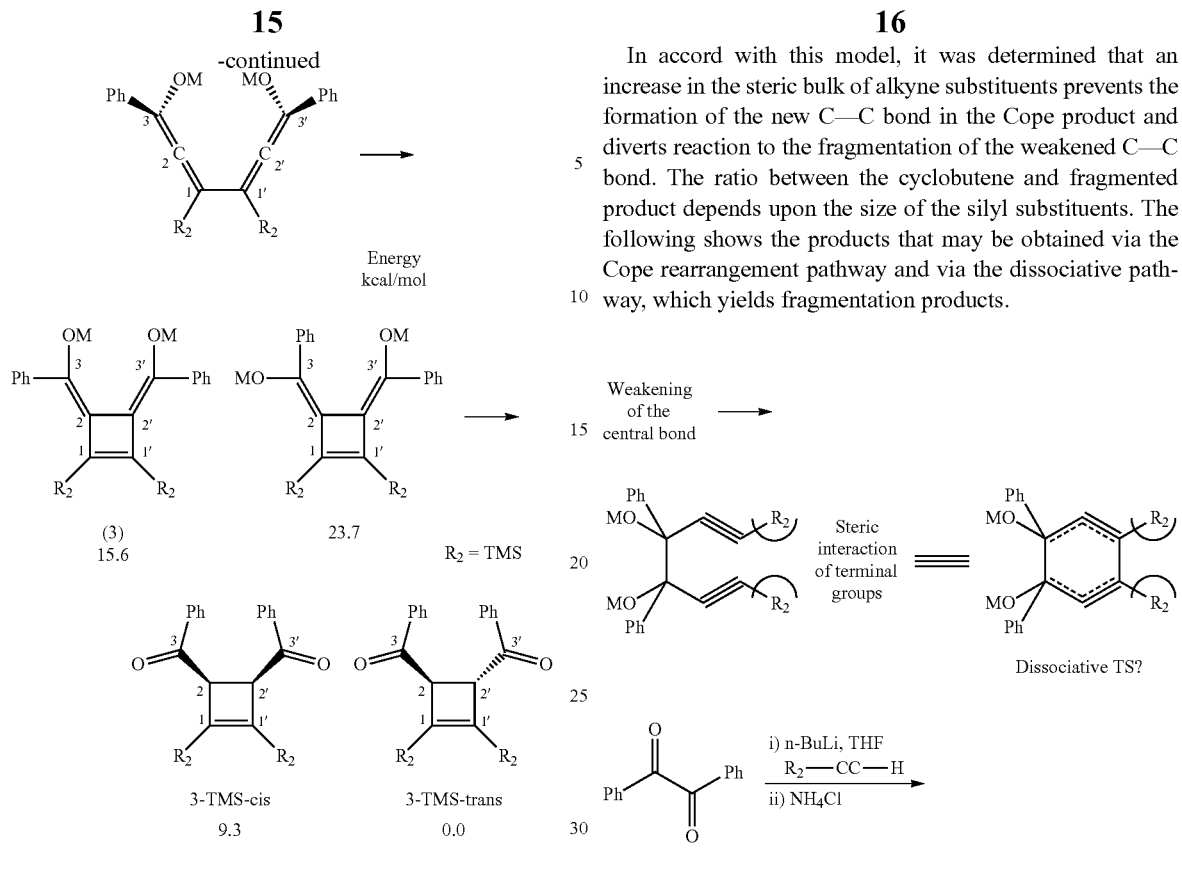

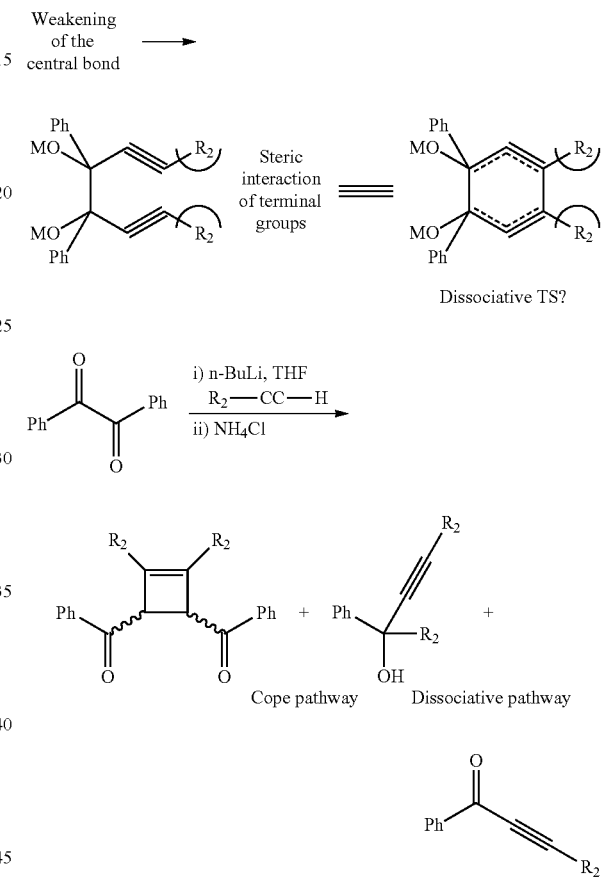

This selectivity suggests that kinetic protonation of the keto-enol intermediate favors formation of a less stable product. See (a) H. E. Zimmerman, *Acc. Chem. Res.* 1987, 20, 263. (b) H. E. Zimmerman, A. Pushechnikov, *Eur. J. Org. Chem.* 2006, 3491. The cis-isomer can be epimerised quantitatively into the more stable trans 3-TMS isomer under basic conditions (stirring with the LiOH/THF/$H_2O$ system or keeping the reaction mixture for 6 hrs at ~pH 9).

The Cope rearrangement step is expected to be highly asynchronous due to the accumulative weakening of the central C—C bond by four substituents: the two anionic oxygens and the two Ph groups. See Scheme 4. Related anionic rearrangements have been suggested to proceed through a dissociative mechanism via the central bond cleavage based on quantum-mechanical computations. See (a) K. A. Black, S. Wilsey, K. N. Houk, *J. Am. Chem. Soc.* 1998, 120, 5622. (b) Y. Y. Hi, K. N. Houk, *J. Am. Chem. Soc.* 1998, 120, 205. (c) K. A. Black, S. Wilsey, K. N. Houk, *J. Am. Chem. Soc.* 2003, 125, 6715.

In accord with this model, it was determined that an increase in the steric bulk of alkyne substituents prevents the formation of the new C—C bond in the Cope product and diverts reaction to the fragmentation of the weakened C—C bond. The ratio between the cyclobutene and fragmented product depends upon the size of the silyl substituents. The following shows the products that may be obtained via the Cope rearrangement pathway and via the dissociative pathway, which yields fragmentation products.

Although cyclobutenes are major products for $R_2$=TMS, a mixture of cyclobutene and fragmented product is formed when two equivalents of triethylsilyl-acetylide (TES-acetylide) are used. See the following reaction Scheme 5.

SCHEME 5:

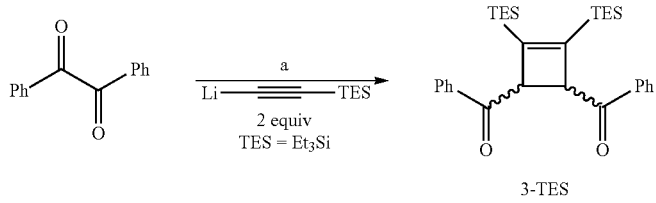

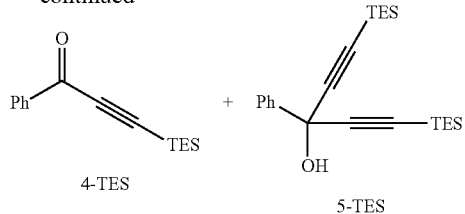

4-TES            5-TES a = i) n-BuLi, THF, TES—C≡CH, ii) NH$_4$Cl
1.0 equiv 4-TES (major) 45%
2.0 equiv 3-TES + 5-TES S = 75%
        3-TES:5-TES = 1.6:1

The fragmentation path becomes dominant for $R_2$=tris-isopropylsilyl-acetylide (TIPS-acetylide) where only ketone 4-TIPS and alcohol 5-TIPS were obtained in ratios dependent upon the amount of lithium acetylide (SI part). See the following reaction Scheme 6. Large excess of acetylide led to the formation of 5-TIPS, while ketone 4-TIPS was formed major products with two equivalents of acetylide. The structure of fragmented products has been confirmed by their independent synthesis but the exact mechanism for their formation remains unclear. The bis-alkyne alcohol was synthesized in 89% yield via reaction of 2.2 eq. of TIPS-acetylide with ethyl benzoate.

SCHEME 6:

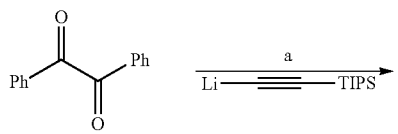

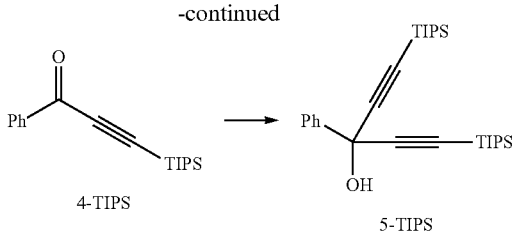

4-TIPS        5-TIPS a = i) n-BuLi, THF, TIPS—C≡CH, ii) NH$_4$Cl

| Equiv. | 4-TIPS:5-TIPS | Σ, % |
|---|---|---|
| 2 | 4-TIPS | 47 |
| 3 | 1:6.5 | 106 |
| 4.5 | 5-TIPS | 135 |

Minor products isolated from complex reaction mixtures suggest that the reaction includes either an ene-reaction or a retro-pinacol fragmentation, topologically analogous to the Cope rearrangement diverted via a fully dissociative transition state. See Scheme 7. Because rate of the $2^{nd}$ TIPS-acetylide addition to the diketone is relatively slow, an additional fragmentation pathway from the mono-adducts is plausible as well.

Scheme 7.

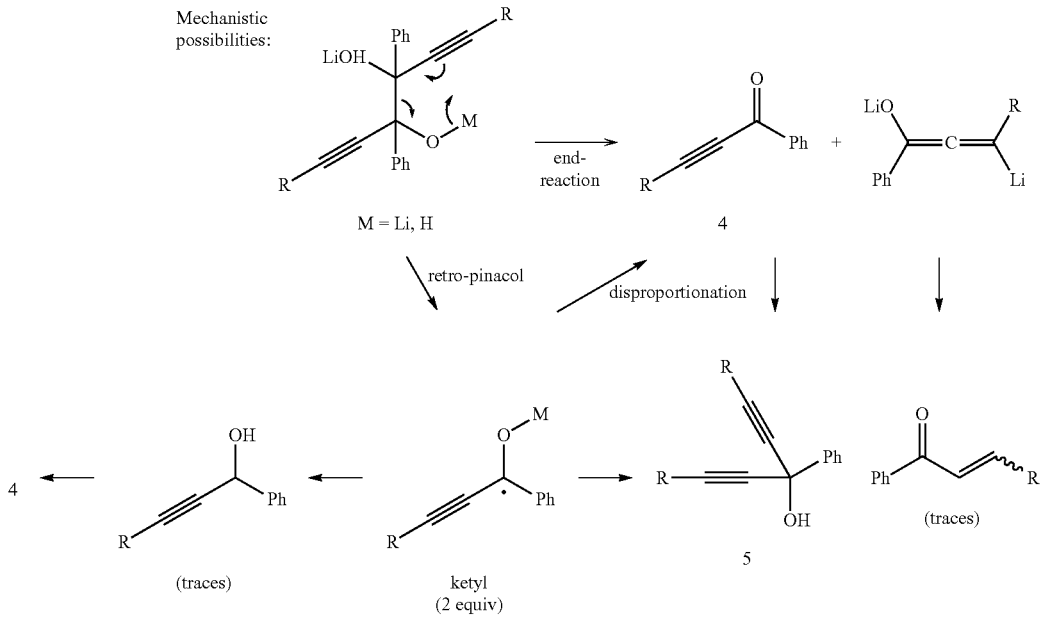

Due to the presence of two hydroxyl groups at the central bond of the bis-alkynes, these compounds can be considered as a latent dicarbonyl functionality which is revealed by the oxy-Cope method in its bis-enolized state. As a result, one can couple the pericyclic step with typical carbonyl chemistry, such as intramolecular aldol condensations. In accord with this notion, reactions of benzil with aryl and alkyl substituted acetylides proceed with the formation of cyclopentenones in 75-85% yield. See the following general Scheme 8 showing the reaction products wherein $R_2$ of the metal acetylide comprises an aryl or alkyl group.

Scheme 8.

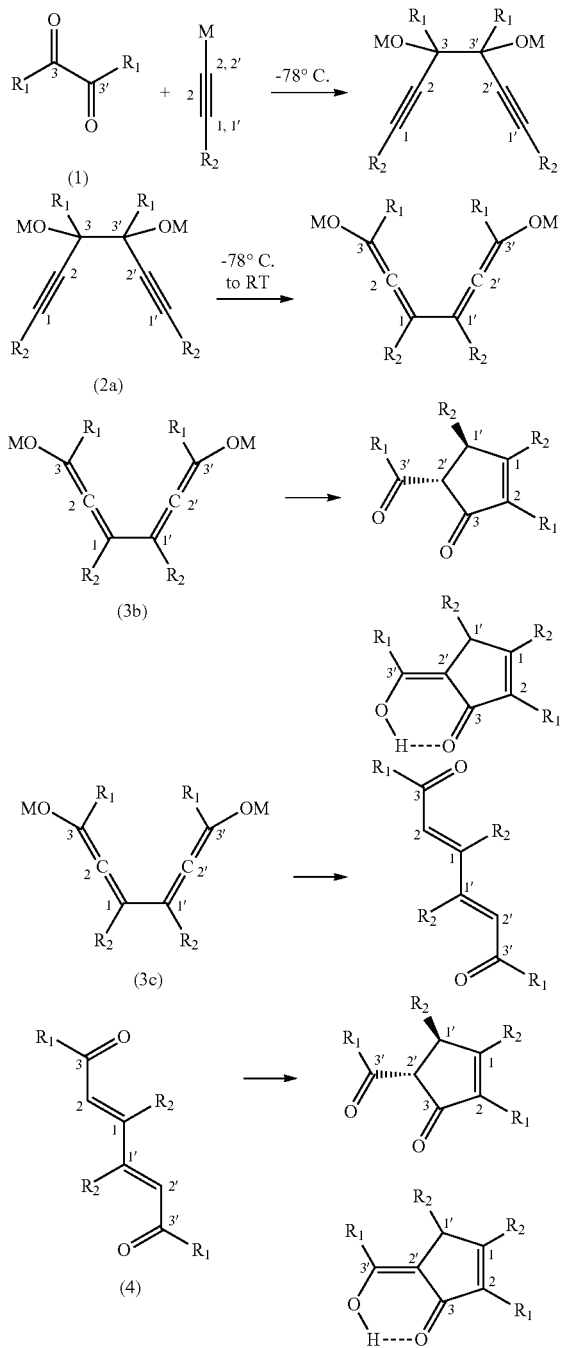

According to some embodiments of the method of the present invention, in order to prepare a cyclopentenone via the rearrangement of a bis-allenic intermediate, the metal acetylide used to form the bis-alkyne precursor (which Oxy Cope rearranges into the bis-allenic intermediate) should be substituted with an alkyl group or an aryl group. In some embodiments, the metal acetylide has the following structure:

wherein M is a counterion, generally an alkali metal cation such as lithium cation, sodium cation, or potassium cation. In preferred embodiments, M is a lithium cation.

In some embodiments, $R_2$ is an alkyl group or an aryl group. The alkyl group generally comprises from 1 to about 18 carbon atoms, such as from 1 to about 6 carbon atoms. The alkyl group may be substituted or unsubstituted. Substituents may include hydroxy, halide, alkyl having from 1 to 6 carbon atoms, alkoxy having from 1 to 6 carbon atoms, amino, nitro, sulfoxide, and cyano. The alkyl group may be substituted with alkoxy generally having from 1 to about 6 carbon atoms. The aryl group may comprise from 6 to 18 carbon atoms, such as from 6 to 10 carbon atoms. The aromatic group may be substituted or unsubstituted. Substituents may include hydroxy, halide, alkyl having from 1 to 6 carbon atoms, alkoxy having from 1 to 6 carbon atoms, amino, nitro, sulfoxide, and cyano.

In some embodiments, the $R_2$ moiety may be selected from among phenyl, tolyl, para-fluorophenyl, and alkyl (e.g., methyl, ethyl, propyl, isopropyl, butyl, pentyl, methoxymethyl, ethoxymethyl, ethoxymethyl, ethoxyethyl and the like).

In embodiments wherein a cyclopentenone is prepared, the α,β-diketone has the general structure:

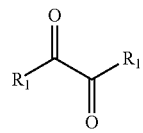

wherein $R_1$ is a hydrocarbyl generally having from 1 to about 18 carbon atoms, preferably from 1 to about 12 carbon atoms, more preferably from 1 to about 6 carbon atoms. The hydrocarbyl may be an alkyl, alkenyl, alkynyl, cycloalkyl, aryl, or alkylaryl. Exemplary $R_1$ groups include methyl, phenyl, ethyl, n-propyl, isopropyl, n-butyl, isobutyl, tert-butyl, pentyls, hexyls, and cyclohexyls. The hydrocarbyls may be substituted or unsubstituted.

In some embodiments of the present invention, both $R_1$ groups are phenyl, which may be substituted or unsubstituted. Substituents groups on the phenyl may be alkyl, aryl, and alkoxy substituents at any of the ortho-, meta-, and para-positions. In general, the substituents may have from 1 to 12 carbon atoms, preferably from 1 to 6 carbon atoms. Exemplary substituents on the phenyl group include methyl, ethyl, propyl, methoxy, ethoxy, propoxy, and phenyl substituents.

In some preferred embodiments of the method of the present invention, both $R_1$ are phenyl, and the α,β-diketone is 1,2-diphenylethane-1,2-dione (commonly known as benzil), which has the following structure:

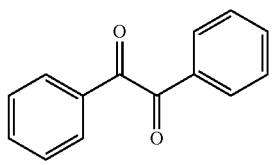 [SMILES: O=C(C(=O)c1ccccc1)c1ccccc1]

In some embodiments, the cyclopentenone compound is prepared via the Oxy Cope rearrangement of a bis-alkyne precursor into the bis-allenic intermediate, which further rearranges into the cyclopentenone compound, as shown in above Scheme 8. In some preferred embodiments, the α,β-diketone is 1,2-diphenylethane-1,2-dione (commonly known as benzil) and the cyclopentenone compounds have the following general structure:

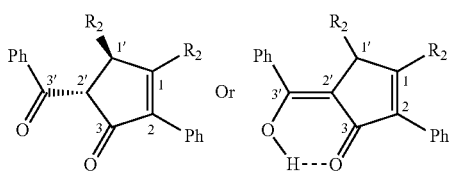

wherein $R_2$ is an alkyl group or an aryl group. The alkyl group generally comprises from 1 to about 18 carbon atoms, such as from 1 to about 6 carbon atoms. The alkyl group may be substituted or unsubstituted. Substituents may include hydroxy, halide, alkyl having from 1 to 6 carbon atoms, alkoxy having from 1 to 6 carbon atoms, amino, nitro, sulfoxide, and cyano. The alkyl group may be substituted with alkoxy generally having from 1 to about 6 carbon atoms. The aryl group may comprise from 6 to 18 carbon atoms, such as from 6 to 10 carbon atoms. The aromatic group may be substituted or unsubstituted. Substituents may include hydroxy, halide, alkyl having from 1 to 6 carbon atoms, alkoxy having from 1 to 6 carbon atoms, amino, nitro, sulfoxide, and cyano.

In some embodiments, the $R_2$ moiety may be selected from among phenyl, tolyl, para-fluorophenyl, and alkyl (e.g., methyl, ethyl, propyl, isopropyl, butyl, pentyl, methoxymethyl, ethoxymethyl, ethoxymethyl, ethoxyethyl and the like).

Figure 1B:
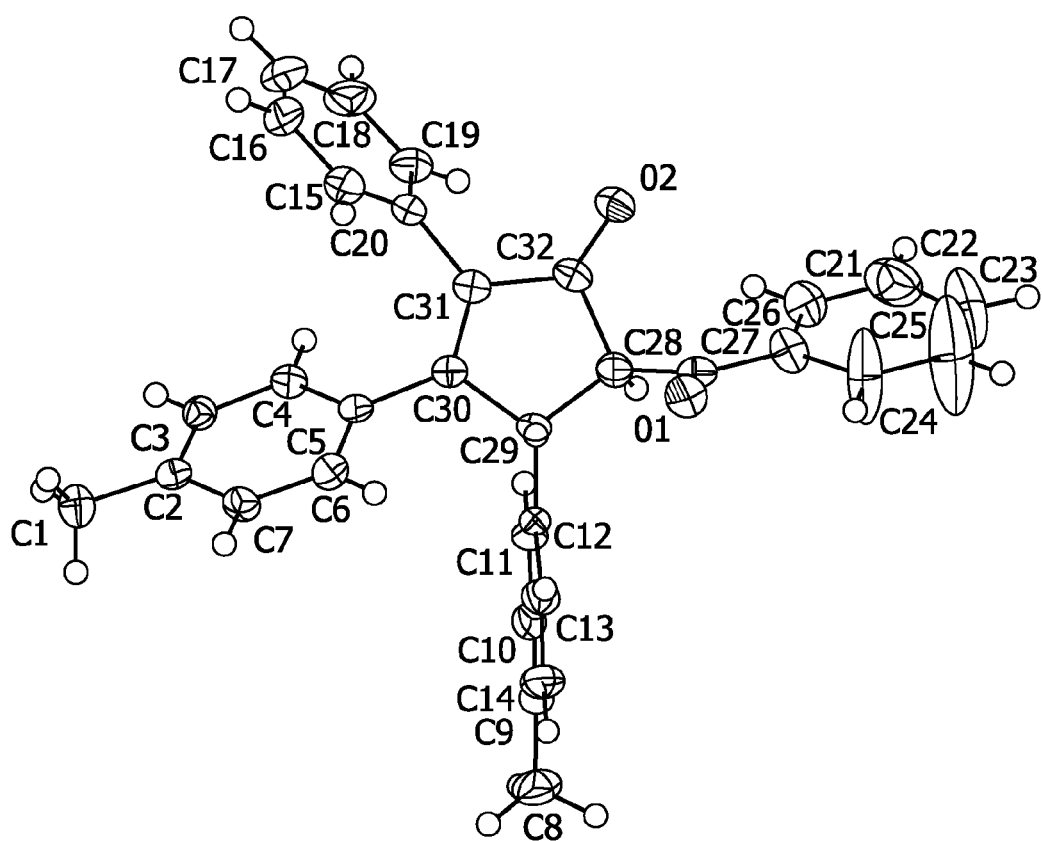
FIG. 1B is an ORTEP diagram for compound 7a prepared according to the method of the present invention.
Figure 1C:
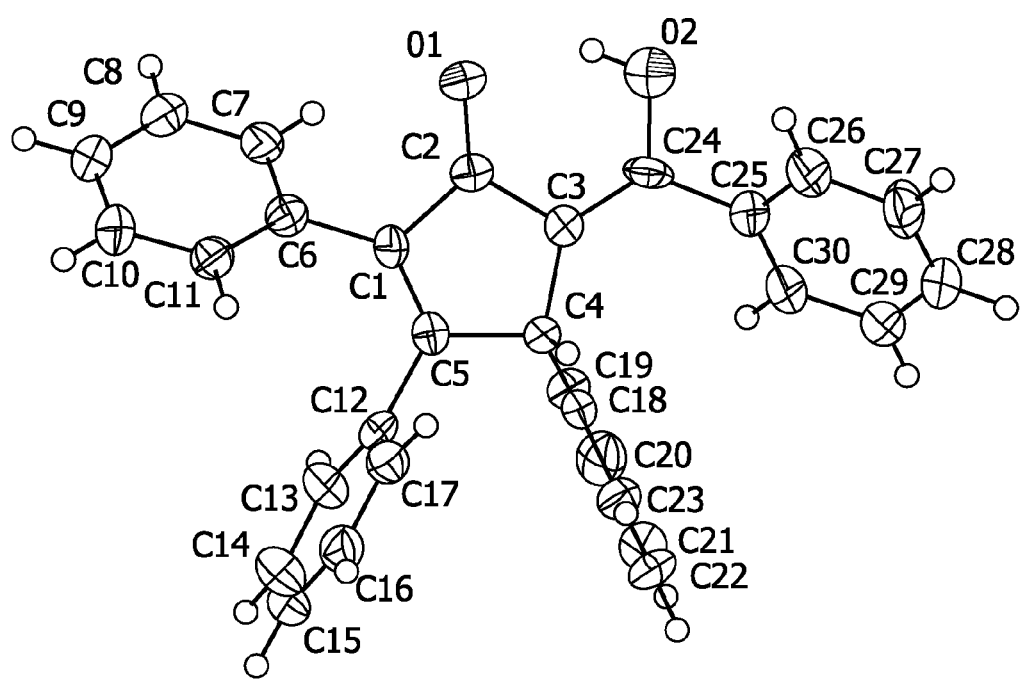
FIG. 1C is an ORTEP diagram for compound 6b prepared according to the method of the present invention.

Scheme 9 demonstrates the cascade for $R_2$ groups phenyl (structure 6A and 6B), tolyl (structure 7A and 7B), and para-fluorophenyl (structure 8A and 8B). The reaction provided a ~2:1 mixture of keto and enol forms of the product which could be separated by fractional crystallisation. See FIGS. 1B and 1C. FIG. 1B is an ORTEP diagram for compound 7a prepared according to the method of the present invention. FIG. 1C is an ORTEP diagram for compound 6b prepared according to the method of the present invention. Neither p-$CH_3$ nor p-F substituents have a large effect on the reaction yield on the keto/enol ratio.

Scheme 9:

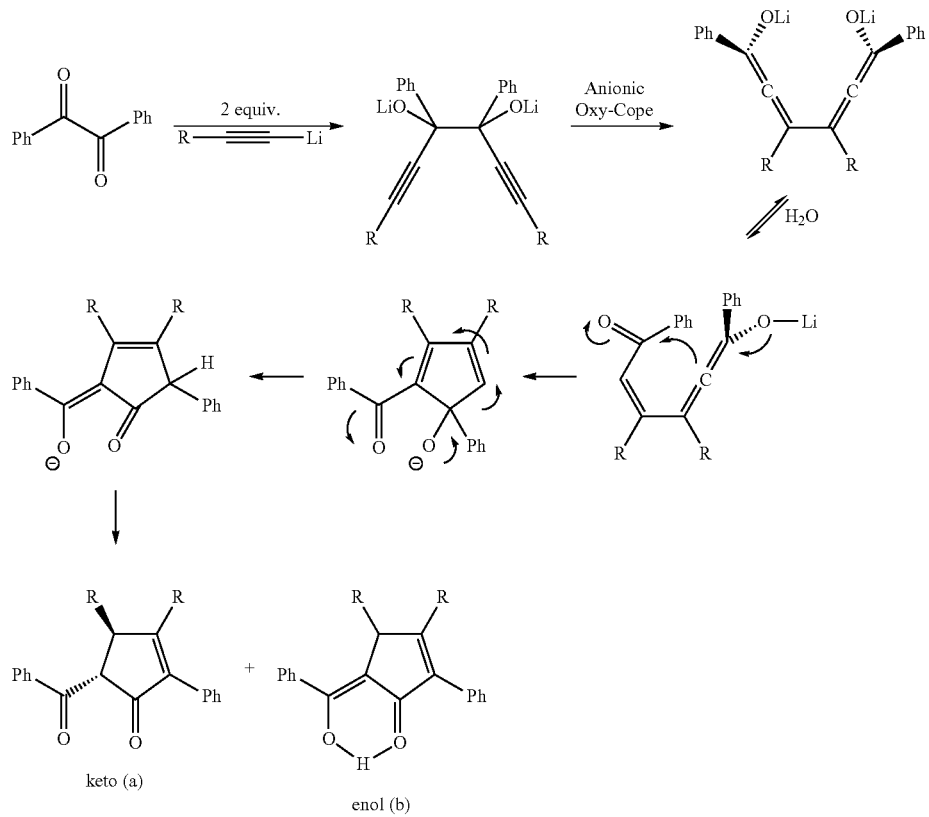

| R | Keto (a):enol (b) | Combined yield (%) |
|---|---|---|
| 6 = Ph, | 2.5:1 | 75 |
| 7 = Tol | 2.3:1 | 78 |
| 8 = p-F-Ph | 2.2:1 | 83 |

Although the reaction with methyl propargyl ether produced the same 5-cyclopentenone framework, the transformation proceeded one step further towards the formation of an exo-cyclic double bond via methanol elimination. In the latter case, the tautomeric equilibrium is shifted towards enol. See Scheme 10.

most stable tautomer in the keto-enol equibrium in the β-diketone (9a) system formed in the reaction of $CH_2OMe$-substituted alkyne.

Figure 1D:
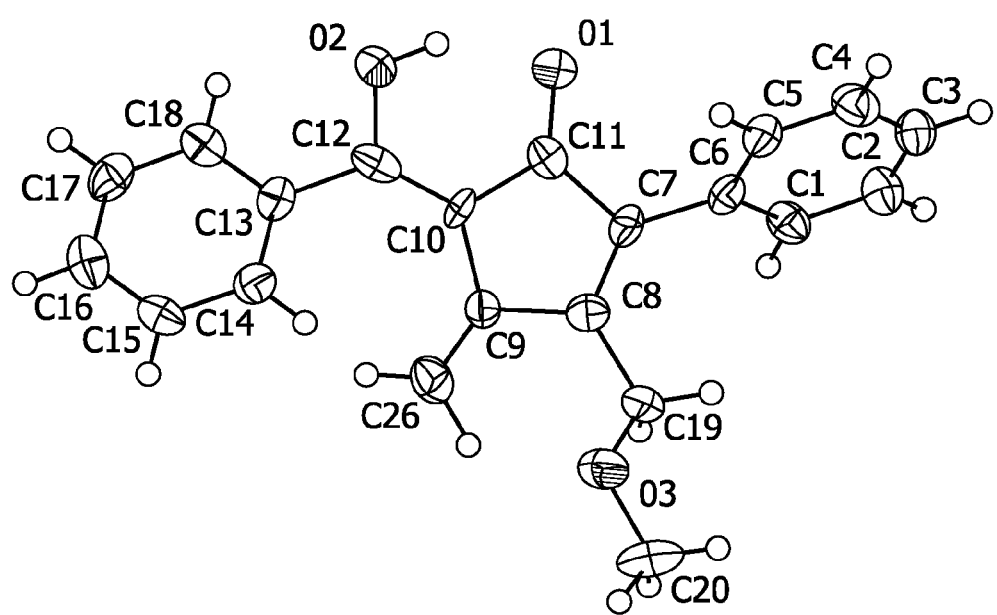
FIG. 1D is an ORTEP diagram for compound 9b prepared according to the method of the present invention.

See Scheme 11. This was observed experimentally. See FIG. 1D for the crystal structure of the enol form. FIG. 1D is an ORTEP diagram for compound 9b prepared according to Scheme 10:

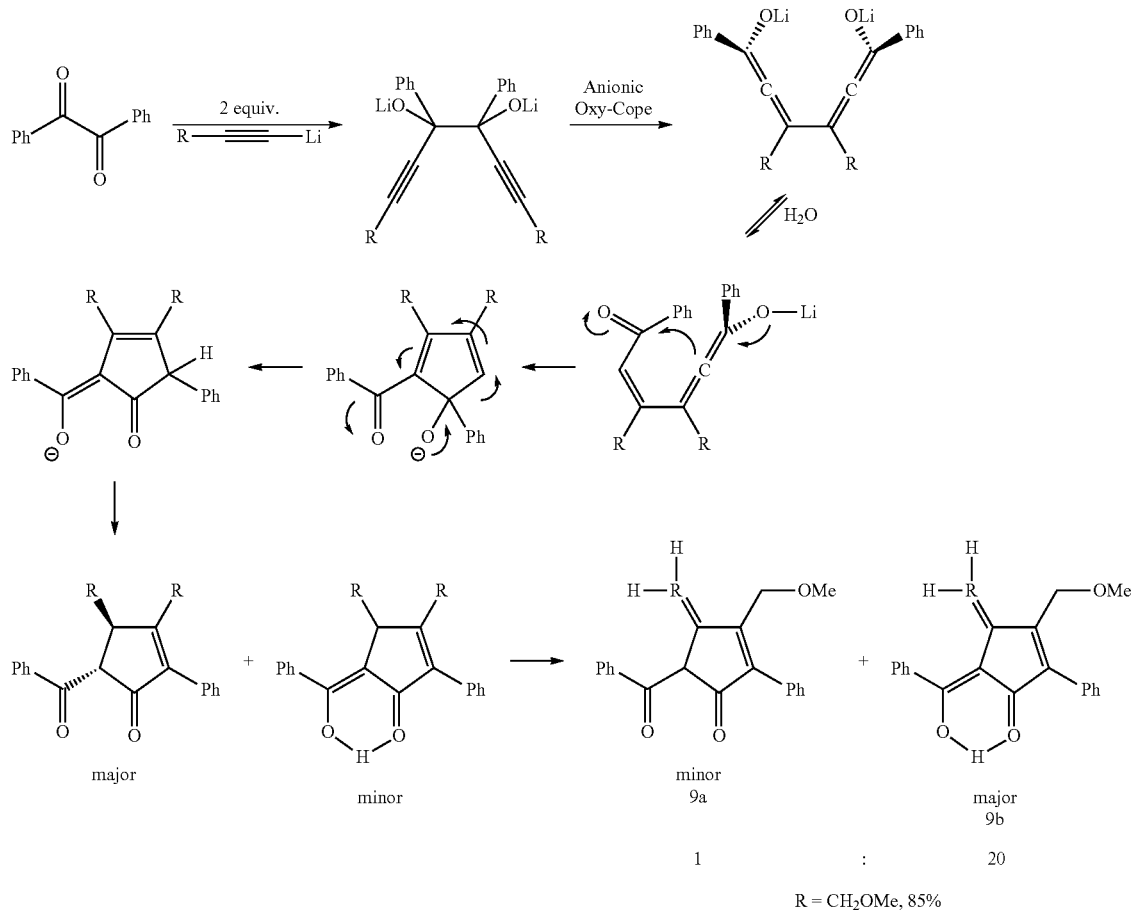

$R = CH_2OMe$, 85%

Path leading to the formation of the cyclopentenones diverges from the same bis-allenic intermediate. Subsequently to the Cope step, aldol condensation closes the cycle in a favorable 5-(enolexo)-exo-trig fashion. See J. E. Baldwin, *Tetrahedron.* 1982, 38, 2939. Due to the high migratory aptitude of the phenyl group in the intermediate, the cyclization is accompanied by a highly exothermic (~32.4 kcal/mol at the B3LYP/6-31+G level) 1,2-phenyl migration and concomitant enolization as depicted in Schemes 9 and 10. The structures of the keto and enol products were unambiguously confirmed by X-ray crystallography. See FIGS. 1B and 1C. Only the trans ketone was isolated, possibly due to the equilibration into the most stable tautomer under the thermodynamic control conditions. The thermodynamic origin of the observed selectivity is supported by the relative energies for the keto and enol products calculated at the B3LYP/6-31+G level. Even though the enol form (6b-8b) is stabilized by a relatively strong Resonance-Assisted Hydrogen Bond (RAHB) with the β-ketone moiety, there is still ~1 kcal/mol thermodynamic preference for the keto form (6a-8a). In contrast, the computations suggest that the enol form (9b) is the the method of the present invention. Neither the cis ketone nor the endocyclic enol, both of which are calculated to be less stable, were detected experimentally.

SCHEME 11:

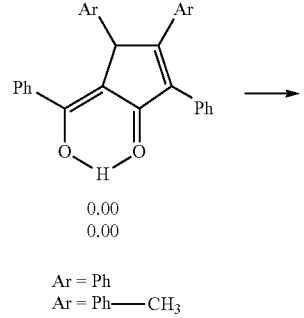

0.00
0.00

Ar = Ph
Ar = Ph——$CH_3$

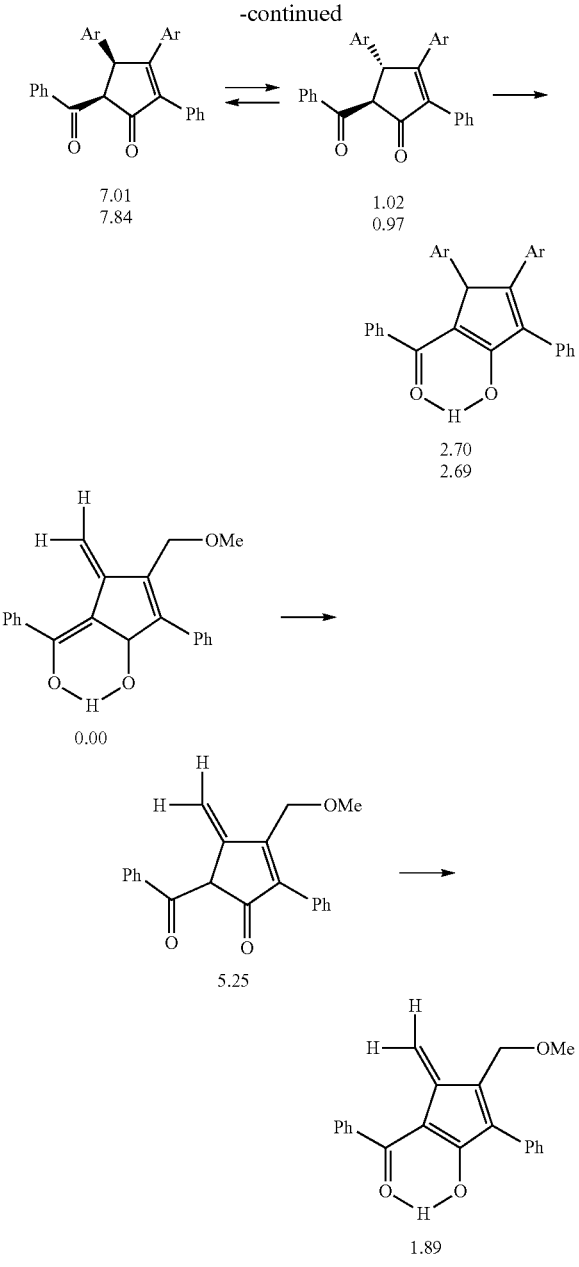

In summary, the present invention is directed to an efficient and convenient procedure for the preparation of cyclobutene and cyclopentenone compounds via a common bis-allenic intermediate. It also allows a conceptually interesting entry in the δ-dicarbonyl chemistry which may enable new approaches to the analogues of such natural products as Rocaglamide and Aglafoline which have shown cytostatic and cytotoxic activity against a variety of human cancer cell lines, with IC50 values in the range 1.0-6.0 ng/mL.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above compositions and methods without departing from the scope of the invention, it is intended that all matter contained in the above description and shown in the accompanying drawings shall be interpreted as illustrative and not in a limiting sense.

What is claimed is:

1. A method of preparing a cyclopentenone compound, the method comprising:
    contacting an α,β-diketone with a metal acetylide at a temperature below 0° C. to thereby form a reaction mixture comprising a bis-alkyne precursor;
    wherein the bis-alkyne precursor rearranges into a bis-allenic intermediate, which undergoes further rearrangement into the cyclopentenone compound as the temperature of the reaction mixture increases from below 0° C. to above 0° C.

2. The method of claim 1 wherein the α,β-diketone and the metal acetylide are contacted at a temperature below about −50° C.

3. The method of claim 1 wherein the rearrangement occurs as the temperature of the reaction mixture increases from about −78° C. to room temperature.

4. The method of claim 1 wherein the α,β-diketone is contacted with the metal acetylide at a molar ratio of metal acetylide to α,β-diketone of at least 1.9:1.

5. The method of claim 1 wherein the metal acetylide has the following structure:

wherein
    M is selected from the group consisting of lithium cation, sodium cation, and potassium cation; and
    $R_2$ is alkyl or aryl.

6. The method of claim 5 wherein $R_2$ is selected from the group consisting of phenyl, tolyl, para-fluorophenyl, and —CH$_2$—O—CH$_3$.

7. A method of preparing a cyclopentenone compound, the method comprising:
    contacting an α,β-diketone with a metal acetylide at a temperature below 0° C. to thereby form a reaction mixture comprising a bis-alkyne precursor, wherein the bis-alkyne precursor has the structure:

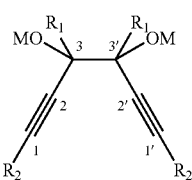

wherein M is selected from the group consisting of lithium cation, sodium cation, and potassium cation; $R_1$ is a hydrocarbyl having from 1 to about 18 carbon atoms; and each $R_2$ is independently alkyl or aryl; and further wherein the bis-alkyne precursor rearranges into a bis-allenic intermediate, which undergoes further rearrangement into the cyclopentenone compound as the temperature of the reaction mixture increases from below 0° C. to above 0° C.

8. The method of claim 7 wherein $R_2$ is selected from the group consisting of phenyl, tolyl, para-fluorophenyl, and —$CH_2$—O—$CH_3$.

9. The method of claim 7 wherein the bis-allenic intermediate has the structure:

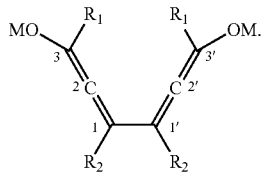

10. The method of claim 7 wherein the cyclopentenone compound has the structure:

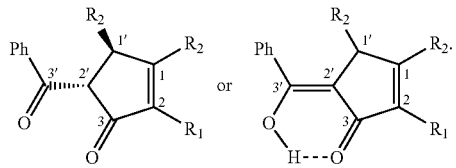

11. The method of claim 7 wherein the α,β-diketone has the following structure:

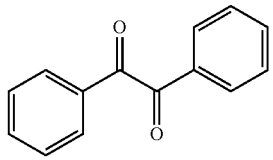 [SMILES: O=C(C(=O)c1ccccc1)c1ccccc1]

12. A method of preparing a cyclopentenone compound, the method comprising:

contacting an α,β-diketone with a metal acetylide at a temperature below 0° C. to thereby form a reaction mixture comprising a bis-alkyne precursor, wherein the bis-alkyne precursor rearranges into a bis-allenic intermediate, which undergoes further rearrangement into the cyclopentenone compound as the temperature of the reaction mixture increases from below 0° C. to above 0° C., wherein the bis-allenic intermediate has the structure:

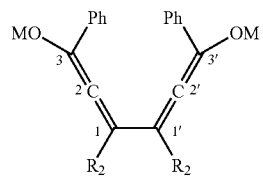

wherein

M is selected from the group consisting of lithium cation, sodium cation, and potassium cation; and each $R_2$ is independently alkyl or aryl.

13. The method of claim 12 wherein $R_2$ is selected from the group consisting of phenyl, tolyl, para-fluorophenyl, and —$CH_2$—O—$CH_3$.

14. The method of claim 11 wherein the cyclopentenone compound has the structure:

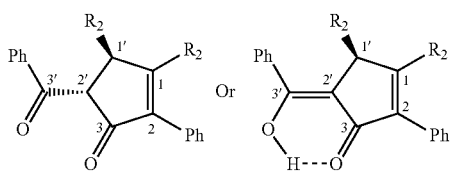

15. The method of claim 1 wherein the α,β-diketone has the following structure:

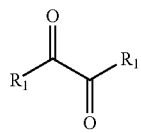

wherein each $R_1$ comprises an aryl.

16. The method of claim 7 wherein the α,β-diketone and the metal acetylide are contacted at a temperature below about −50° C.

17. The method of claim 7 wherein the rearrangement occurs as the temperature of the reaction mixture increases from about −78° C. to room temperature.

18. The method of claim 7 wherein the α,β-diketone is contacted with the metal acetylide at a molar ratio of metal acetylide to α,β-diketone of at least 1.9:1.

19. The method of claim 7 wherein the metal acetylide has the following structure:

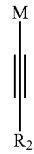

wherein

M is selected from the group consisting of lithium cation, sodium cation, and potassium cation; and $R_2$ is alkyl or aryl.

20. The method of claim 19 wherein $R_2$ is selected from the group consisting of phenyl, tolyl, para-fluorophenyl, and —$CH_2$—O—$CH_3$.

* * * * *